(12) United States Patent
Angelantoni et al.

(10) Patent No.: US 7,527,764 B2
(45) Date of Patent: May 5, 2009

(54) AUTOMATIC SYSTEM FOR CONSERVING SAMPLES AT A CONTROLLED TEMPERATURE

(75) Inventors: Gianluigi Angelantoni, Massa Martana (IT); Pasquale De Blasio, Bruaherio (IT); Andrea Pedrazzini, Segrate (IT); Mauro Zenobi, Umbra (IT)

(73) Assignee: Angelantoni Industrie S.p.A., Massa Martana (PG) (IT)

( * ) Notice: Subject to any disclaimer, the term of this patent is extended or adjusted under 35 U.S.C. 154(b) by 484 days.

(21) Appl. No.: 10/529,285

(22) PCT Filed: Sep. 25, 2003

(86) PCT No.: PCT/EP03/10716

§ 371 (c)(1),
(2), (4) Date: Mar. 25, 2005

(87) PCT Pub. No.: WO2004/028572

PCT Pub. Date: Apr. 8, 2004

(65) Prior Publication Data

US 2005/0260102 A1    Nov. 24, 2005

(30) Foreign Application Priority Data

Sep. 26, 2002   (IT) .......................... BO2002A0607

(51) Int. Cl.
*G01N 35/00* (2006.01)
*B65G 1/12* (2006.01)

(52) U.S. Cl. .......................... 422/65; 422/64; 422/104; 436/45; 221/210; 62/266; 414/331.01; 414/331.02; 414/331.05

(58) Field of Classification Search ........................ None
See application file for complete search history.

(56) References Cited

U.S. PATENT DOCUMENTS

| | | | |
|---|---|---|---|
| 5,233,844 A | 8/1993 | Knippscheer et al. | |
| 5,638,686 A * | 6/1997 | Coelho et al. | 62/51.1 |
| 5,825,507 A * | 10/1998 | Bhatt et al. | 358/403 |
| 6,068,437 A * | 5/2000 | Boje et al. | 414/331.02 |
| 6,245,297 B1 | 6/2001 | Kowallis | |

(Continued)

FOREIGN PATENT DOCUMENTS

WO    WO 98/58216    12/1998

(Continued)

*Primary Examiner*—Jill Warden
*Assistant Examiner*—P. Kathryn Wright
(74) *Attorney, Agent, or Firm*—Fredrikson & Byron, P.A.

(57) ABSTRACT

An automatic system (100) for conserving samples at a controlled temperature comprising at least one controlled-temperature thermo-insulated conservation chamber (1) with temperature control means (3) containing a set of disks (9) for storing samples (19) and a Cartesian robotic system (4) equipped with pick-up device (18), contained in an upper chamber (2) separated from the chamber (1) by means of an insulating shelf (6), where said Cartesian system (4) through the controlled-access opening (7) moves the samples (19) between the I/O drawer (20) and the above-mentioned set of disks (9). The combined and synchronized movement of the robotic device (4) and of every single disk of the set enables each storage location to be reached. The management of the devices of the automatic system (100) is controlled by an N/C system driven by dedicated management SW.

22 Claims, 3 Drawing Sheets

U.S. PATENT DOCUMENTS

| | | |
|---|---|---|
| 6,302,327 B1 | 10/2001 | Coelho et al. |
| 2003/0118487 A1* | 6/2003 | Pressman et al. ............ 422/104 |
| 2004/0213651 A1* | 10/2004 | Malin .................... 414/331.05 |
| 2008/0213080 A1* | 9/2008 | Cachelin et al. .......... 414/791.6 |
| 2008/0231152 A1* | 9/2008 | Malin ........................ 312/305 |

FOREIGN PATENT DOCUMENTS

| WO | WO 01/54817 A2 | 8/2001 |
|---|---|---|

* cited by examiner

AUTOMATIC SYSTEM FOR CONSERVING SAMPLES AT A CONTROLLED TEMPERATURE

CROSS-REFERENCE TO RELATED APPLICATIONS

The present application claims priority to International Application No. PCT/EP03/10716 filed 25 Sep. 2003, which in turn claims priority to Italian Patent Application No. B02002A000607, filed 26 Sep. 2002, the teachings of all of which are incorporated herein by reference in their entirety.

The present invention comes within the sector of conservation devices and in particular refers to an automatic system for conserving samples in general and, in particular, biological samples at a controlled temperature.

Thermostatic devices are known for the conservation of samples of biological material at low temperature, which consist of freezers of the so-called horizontal type with opening from above and vertical type with front opening.

In said known devices the samples are conserved in containers, generally of small dimensions, positioned manually in baskets or supports moved manually.

The solutions that are available today are only controlled manually and have the following serious limitations:

Human errors in manipulating,

Human errors in identifying the samples,

Exposure of the operators to the risks of biological contamination and burning in the event of accidental contact with low temperature parts.

Intolerable slowness of the manual processes and consequent high managing costs.

The object of the present invention is to propose a system for the controlled-temperature conservation of samples, in particular of the biological type, which is capable of automatically moving said samples, in input and output, eliminating the above-mentioned limitations.

The object of the present invention is achieved in accordance with the contents of the claims.

The characteristics of the invention are highlighted with particular reference to the enclosed sheets of drawings, in which.

Figure 1:
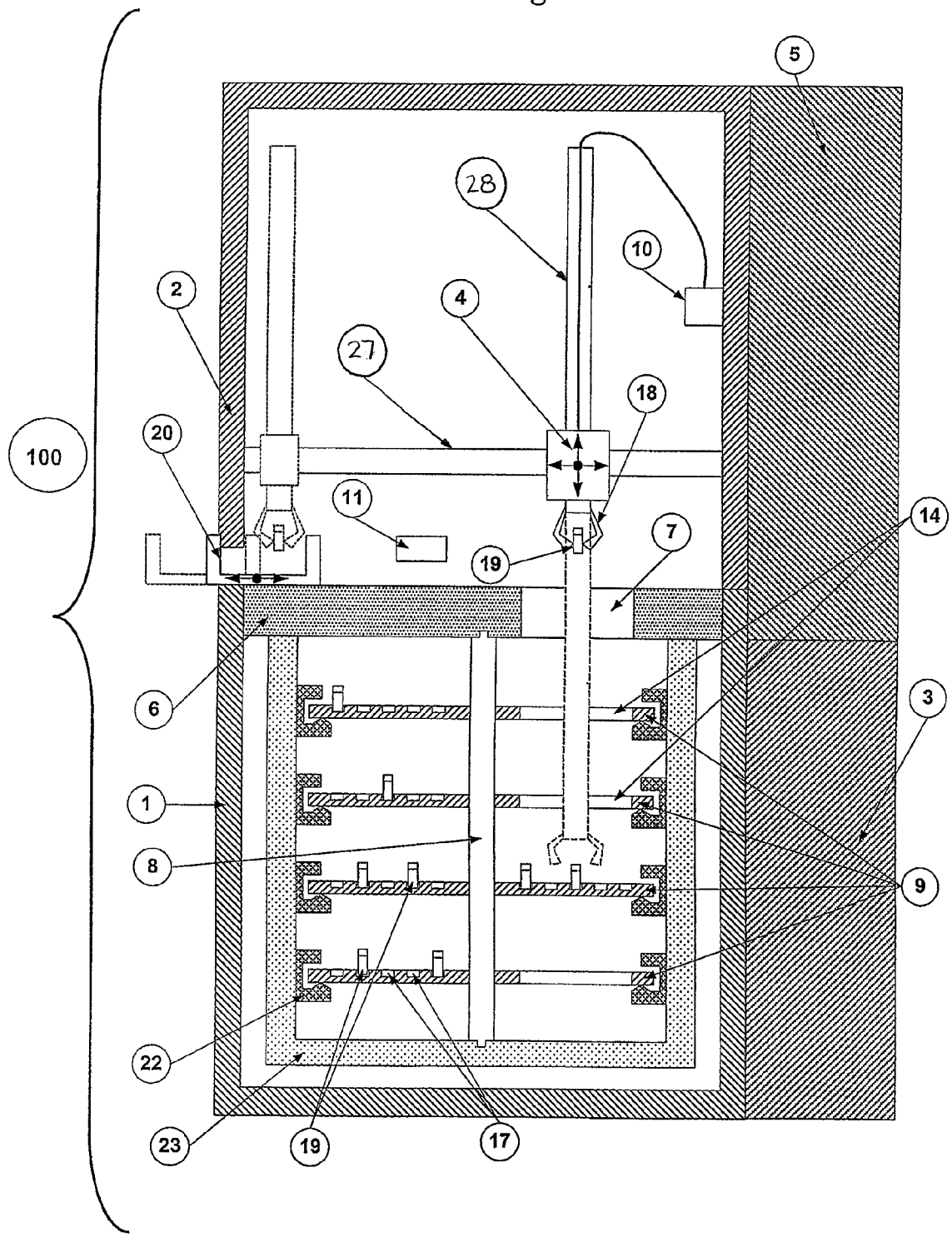
FIG. 1 illustrates a side schematic view of the device of the present invention, in which several parts have been partially or totally removed to highlight others better.
Figure 2:
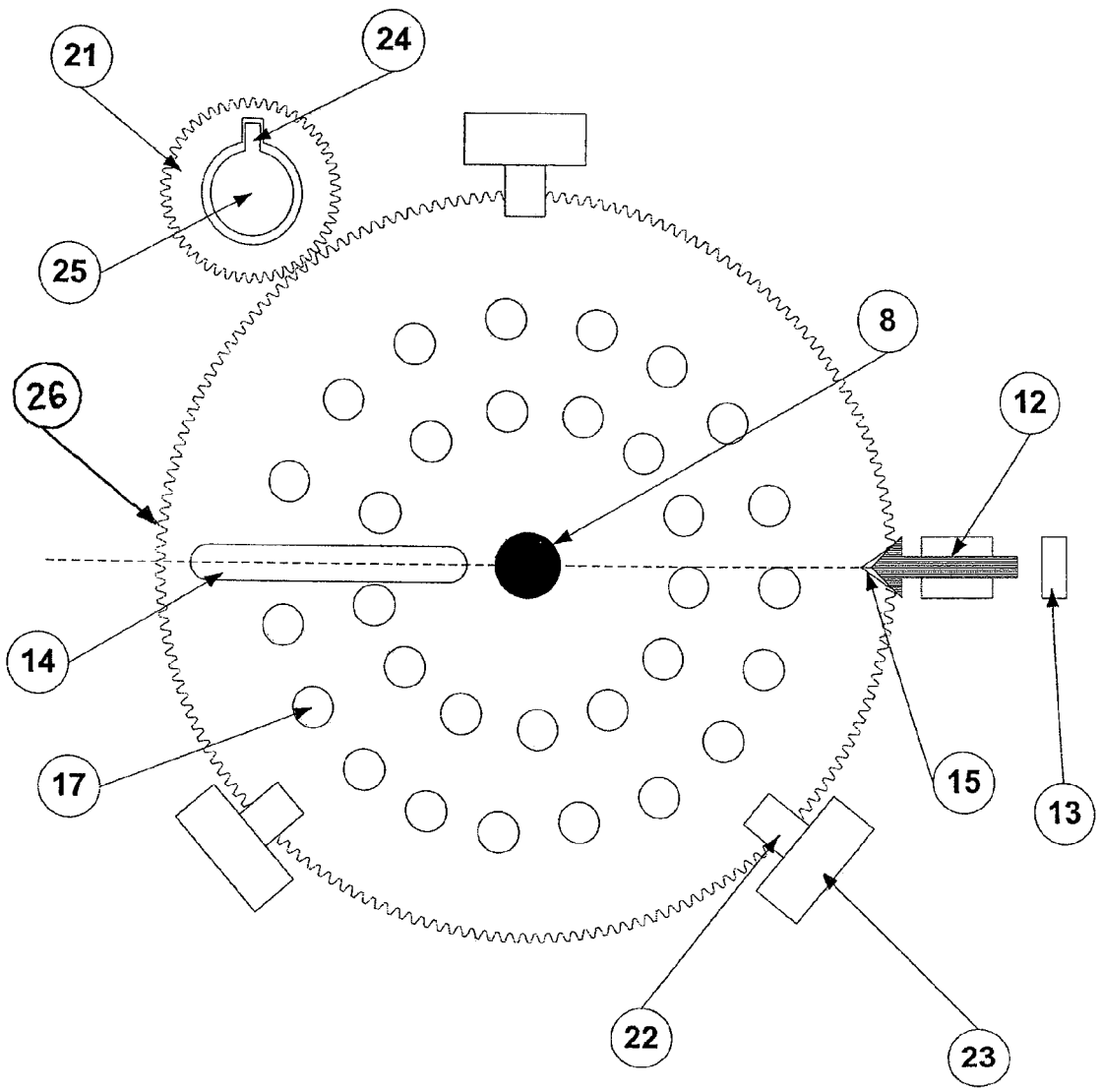
FIG. 2 illustrates a section of the system illustrated in FIG. 1 made with a horizontal plane.
Figure 3:
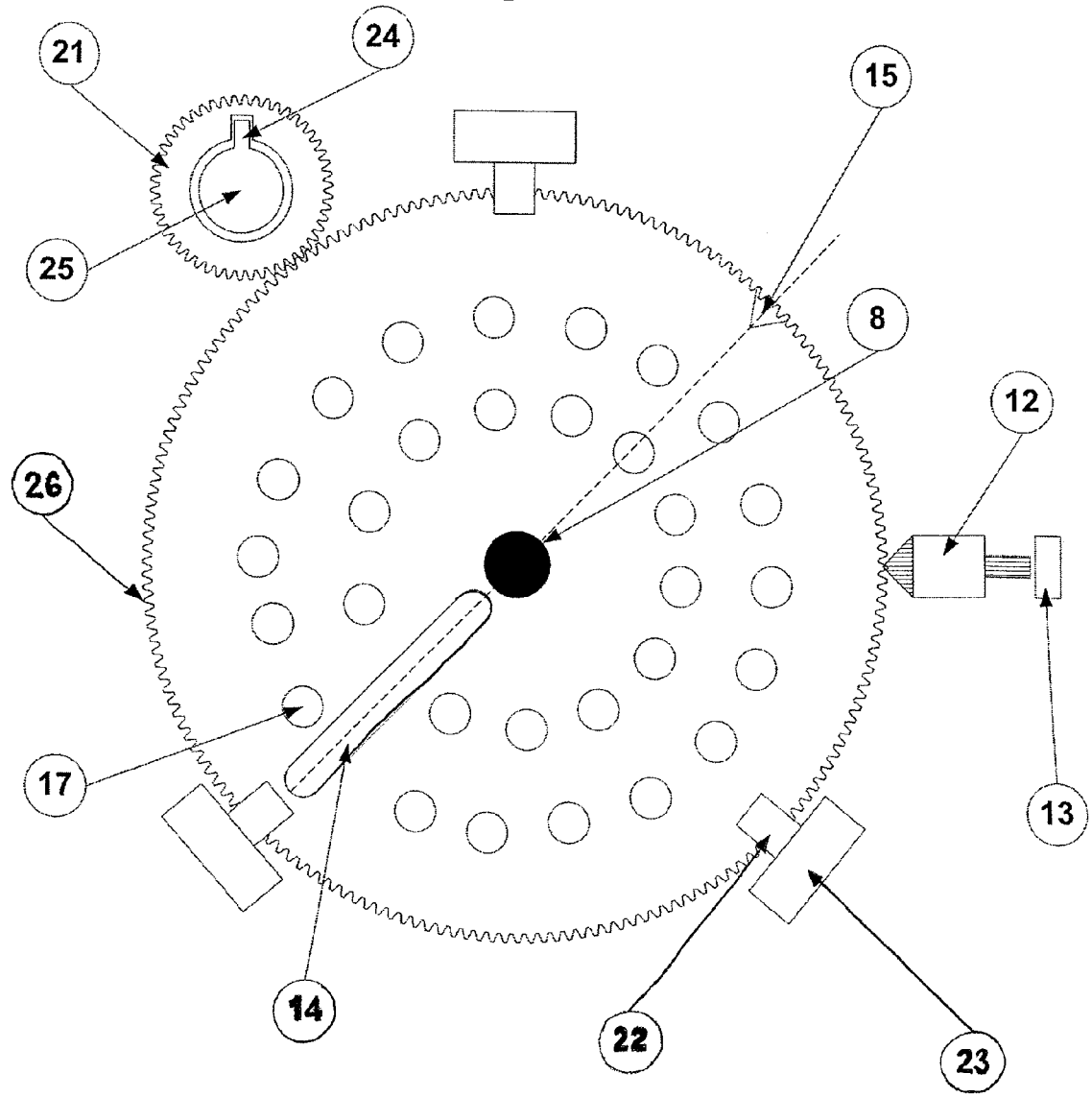
FIG. 3 illustrates the same section as FIG. 2 with the disk rotated by a certain angle.

System 100 is mainly constituted by an assembly of two chambers 1 and 2 separated horizontally by a thermally insulated shelf 6 and functionally connected to each other, that have the aim, the first 1, positioned below, to contain the samples at controlled temperature and the second 2, positioned above the first, to contain, at ambient temperature, means for moving the samples between the two chambers and from the upper chamber towards the outside and vice versa.

The lower chamber is fitted with means 3 that control its temperature and which, as a non-limitative example, are positioned on a side of the same chamber.

In the same manner the upper chamber 2 is equipped with means 5 for controlling the robotized movement systems of the samples, which, as a non-limitative example, are positioned on a side of the same chamber.

Chamber 1 contains a stack of disks 9 totally centered on an axis 8 on which the locations 17 of the samples 19 are positioned.

The disks are supported individually by a group of three peripheral supports 22 positioned on three corresponding vertical uprights 23 connected to each other mechanically at 120°, so that the weight of each disk is born on its own supports 22 identically for all the disks.

Each disk is characterized in that it has a radial slot 14 associated to a zero notch such that the alignment on the notch itself ensures the consequent alignment of the slots of the disks on the same vertical. The disks 9 in position "0" have radial slots 14 on the same vertical as the controlled access opening 7 made on the shelf 6 of separation between chamber 1 and chamber 2. Said vertical alignment enables the Cartesian system 4 to vertically penetrate the entire stack of disks with its pick-up device 18.

For the above the pick-up device 18 can reach any location laying on a previously rotated disk, passing through, sequentially, the opening 7 positioned on the insulating shelf 6 and all the radial slots 14 of the disks above the disk containing the location concerned. Therefore the sample 19 can be picked up or deposited in said location.

The "0" device 12 with which each single disk is provided immobilises in the position "0" all the disks except that containing the location concerned in the loading or unloading operation of sample 19; said disk rotates around axis 8 until it positions location 17 concerned on the vertical of the controlled access opening 7.

The position sensor 13, with which every single "0" 12 device is equipped, ensures that the position of the devices stopping the disks 9 is monitored, so that only the disk containing the location involved in loading or unloading is rotated starting from position "0".

At the same time a disk from the stack 9 containing the location to load or unload is released the corresponding device 21 is activated, starting the rotation of the disk until it presents the location involved on the vertical of the pick-up device 18 of the Cartesian robotic system 4.

As a non-limitative example the device 21 for the rotation of each disk can be made by a toothed wheel geared by command, by means of the device 24 on a motorized axis 25. The angular position of said motorized shaft 25 is monitored by an encoder of suitable resolution. Said toothed wheel 21 permanently engages a toothing position on the periphery 26 of its corresponding disk of the stack 9.

The upper chamber 2 separated from the chamber 1 by the insulation shelf 6 also contains, in addition to the already mentioned robotic system 4, the system for identifying the sample 11, the optical sensor 10, the I/O drawer for the input/output of the samples 19.

The main aim of the separation produced by the insulation shelf 6 is to maintain all the devices contained in the chamber 2 at ambient temperature so that they can be subjected to maintenance without interfering with the controlled-temperature chamber 1.

As non-limitative example, the robotic system 4 includes at least two numerical control rails. The system 4 is composed of a skid, movable along a horizontal rail 27, which, in turn, conveys a vertical rail 28 that is fitted with pick-up device 18 and the end part of an optical sensor 10 to obtain a return signal of the precision of the positioning of the gripper 18 in relation to the location 17. As shown in FIG. 1, the horizontal rail 27 extends entirely across the stacked disks 9, with a portion thereof extending above the opening 7 of the shelf 6.

As non-limitative example said optical sensor 10 can be made with an optical fiber device or with microcamera.

The combined electronic control of the movement of the disks and of the robotic system enables the locations of the samples to be managed automatically.

A fundamental feature of this automatic managing system 100 for the controlled-temperature conservation of samples is to establish an unequivocal connection between the storage location 17 and the sample 19 by using a procedure for identifying the sample with means 11 placed inside chamber 2 so that it is possible, in input or in output, to confirm the identity of the sample being moved.

As non-limitative example the identification system 11 can be a barcode reader, a tag reader, or preferably an identification device of a two-dimensional code marked directly on the surface of the sample.

The input and the output of the samples takes place using an I/O drawer 20 that places in communication, upon command, the external world with the upper chamber 2. The characteristic of the drawer 20 is that it forms a seal between the chamber 2 and the external world so that, both in the open position and in the closed position, the entrance of humid external air into chamber 2 is limited at a maximum extent.

The loading operation comes about by commanding the opening of the drawer that can be in this manner loaded with one or more samples. With the closing of the drawer the samples are transferred inside chamber 2 where the robotized system 4 picks up each sample with the pick-up device 18 and, after the identification process carried out with device 11 deposits it in the required location.

The sample unloading operation comes about carrying out the operations described above in reverse order.

As non-limitative example the movement of the drawer 20 can be obtained by means of a pneumatic piston and the "open" and "closed" positions are monitored by special sensors.

The automatic management system 100 for the controlled-temperature conservation of samples makes use of a control system consisting of SW and HW modules whose main components are the following:

HW Components:
Electronic systems for piloting the axes, the sensors and the ID sensors,
Electromechanical devices for the movement of the axes of the system,
SW components:
Graphic interface with the operator,
Management data base of the locations and the samples,
Driver for the control of the axes,
Robotic programs,
Communication protocols between the internal devices, between each other and towards the external world,
System diagnostics,
Devices for remote control.

The invention described above is intended as being a non-limitative example, therefore any constructive variations come within the protective framework of the present technical solution, as described above and hereinafter claimed.

The invention claimed is:

1. An automatic system for the storage of samples comprising a lower chamber wherein a stack of disks independently rotatable around a vertical axis is arranged, said disks being provided with locations for storing the samples and with radial slots, the lower chamber in selective communication only with an upper chamber located above and separated from the lower chamber by means of a shelf fitted with an opening, the upper chamber in selective communication with external world only by an I/O drawer,
characterized by a Cartesian robotic system disposed in the upper chamber and configured to direct a pick-up device in horizontal and vertical directions only, the system comprising a horizontal rail that extends entirely across the stacked disks with a portion of the horizontal rail extending above the opening of the shelf and a vertical rail movable along the horizontal rail and along which the pick-up device can move into and out of the lower chamber for loading or unloading the samples wherein, when the pick-up device moves into and out of the lower chamber for loading or unloading the samples, the radial slots of the disks which are above one of the disks bearing the location of a chosen sample, are vertically aligned with the opening.

2. System according to claim 1, wherein the lower chamber is a controlled temperature thermo-insulated chamber.

3. System according to claim 1, wherein the shelf is a thermally insulated shelf.

4. System according to claim 1, wherein the opening is a controlled access opening.

5. System according to claim 4, wherein the controlled-access opening is fitted with bodies that keep said opening closed so that the bodies open said opening only when the sample pick-up device is required to pass there through.

6. System according to claim 1, wherein the opening has a length at least equivalent to a maximum radial distance between two samples on same disk.

7. System according to claim 1, wherein the radial slot has a length at least equivalent to a maximum radial distance between two samples on same disk.

8. System according to claim 1, wherein every disk of the stack is held by a group of three supports positioned at 120 degrees along a periphery of each single disk.

9. System according to claim 1, wherein each single disk, and only one disk at a time, can be rotated by means of a device, which couples on a corresponding periphery of each disk.

10. System according to claim 9, wherein a complex of toothed wheels always in contact on a peripheral toothing of the corresponding disks and of a engaging device integral with a motorized shaft which is suitably commanded places in rotation only one toothed wheel and thus the corresponding disk of the stack.

11. System according to claim 10, wherein the one disk of the stack that is placed in rotation by the device is monitored in its angular position by means of an encoder mounted on the motorized pulling shaft.

12. System according to claim 1, wherein all the disks are held blocked by an "0" device with the slots aligned vertically, except for the one disk whose rotation brings the location under said slots.

13. System according to claim 12, wherein the "0" device is fitted with a sensor capable of monitoring the position of said "0" device and, at the same time, an "0" position of each disk held blocked.

14. System according to claim 1, wherein the upper chamber contains a device for identifying the samples input to and output from the system.

15. System according to claim 1, wherein the operations of inserting and extracting the samples from the system comes about by means of the I/O drawer that connects the external world with the upper chamber containing, amongst other things, the robotic device.

16. System according to claim 1, wherein the samples are accessible from the lower chamber only by means of the robotized system.

17. System according to claim 1, wherein the pick-up device of the sample is equipped with an optical sensor for monitoring correct positioning of said pick-up device in relation to the location of the chosen sample.

18. System according to claim 1, wherein the robotic system, a system for identifying the sample, an optical sensor and the I/O drawer are contained in the upper chamber permitting maintenance activity to be carried out on said robotic system, said system for identifying the sample, said optical sensor and said I/O drawer without interfering with the controlled-temperature chamber.

19. System according to claim 1, wherein the entire management of the devices of the system is controlled by a control system driven by a dedicated management SW.

20. System according to claim 1, wherein the robotized system is controlled by a SW that records every operation set up by an operator and carried out by the system.

21. System according to claim 1, wherein the vertical rail is operatively connected with the horizontal rail, wherein such operative connection enables the vertical rail being movable along the horizontal rail.

22. System according to claim 21, wherein the vertical rail is fitted with the pick-up device.

* * * * *